United States Patent
Petersen

(10) Patent No.: US 9,125,582 B2
(45) Date of Patent: Sep. 8, 2015

(54) ENDOSCOPE HAVING A CAMERA HOUSING AND METHOD FOR MAKING A CAMERA HOUSING

(75) Inventor: Lasse Kjeld Gjoeske Petersen, Frederiksvaerk (DK)

(73) Assignee: AMBU A/S, Ballerup (DK)

( * ) Notice: Subject to any disclaimer, the term of this patent is extended or adjusted under 35 U.S.C. 154(b) by 138 days.

(21) Appl. No.: 13/133,692

(22) PCT Filed: Dec. 9, 2009

(86) PCT No.: PCT/EP2009/066728
§ 371 (c)(1),
(2), (4) Date: Aug. 12, 2011

(87) PCT Pub. No.: WO2010/066790
PCT Pub. Date: Jun. 17, 2010

(65) Prior Publication Data
US 2011/0288372 A1    Nov. 24, 2011

(30) Foreign Application Priority Data

Dec. 10, 2008  (DK) .................................. 2008 01759

(51) Int. Cl.
*A61B 1/00*    (2006.01)
*H04N 5/225*  (2006.01)
(Continued)

(52) U.S. Cl.
CPC .............. *A61B 1/051* (2013.01); *A61B 1/0008* (2013.01); *A61B 1/0011* (2013.01);
(Continued)

(58) Field of Classification Search
CPC .................. A61B 1/0011; A61B 1/05

USPC .................. 600/109, 129, 920; 348/373–376;
264/269, 275; 425/543–544, 571, 577
IPC .................................. A61B 1/0011,1/05, 1/008
See application file for complete search history.

(56) References Cited

U.S. PATENT DOCUMENTS

| | | | |
|---|---|---|---|
| 4,706,653 A | 11/1987 | Yamamoto | |
| 4,745,470 A | 5/1988 | Yabe et al. | |

(Continued)

FOREIGN PATENT DOCUMENTS

| | | | |
|---|---|---|---|
| CN | 1409147 A | 4/2003 | |
| CN | 1794944 A | 6/2006 | |

(Continued)

OTHER PUBLICATIONS

JP 2005-152043 English machine Translation, Espacenet.com and JP Patent & Utility Model Gazette DB, 22 pages.*

(Continued)

*Primary Examiner* — John P Leubecker
*Assistant Examiner* — Arnaldo Torres Diaz
(74) *Attorney, Agent, or Firm* — Faegre Baker Daniels LLP

(57) ABSTRACT

The current invention relates to a method for making a camera housing of an endoscope having a camera housing arranged at the distal end of the insertion portion, said camera housing being a molded component comprising an outer surface, a camera device embedded in the material of the camera housing, a light source embedded in the material of the camera housing, an opening at the distal end of the camera housing, and a channel in fluid communication with said opening. The endoscope further comprises a tube which provides fluid communication between the channel in the camera housing to the proximal end of the endoscope. The endoscope further comprises a bending portion arranged at the distal end of the insertion portion and at the proximal end of the camera housing and where the most distal portion of the bending portion is embedded in the material of the camera housing.

19 Claims, 10 Drawing Sheets

(51) Int. Cl.
*B29C 45/14* (2006.01)
*A61B 1/05* (2006.01)
*A61B 1/005* (2006.01)
*A61B 1/015* (2006.01)
*A61B 1/06* (2006.01)

(52) U.S. Cl.
CPC .......... *A61B 1/0051* (2013.01); *A61B 1/0057* (2013.01); *A61B 1/00066* (2013.01); *A61B 1/00091* (2013.01); *A61B 1/00096* (2013.01); *A61B 1/015* (2013.01); *A61B 1/05* (2013.01); *A61B 1/0676* (2013.01); *A61B 1/0684* (2013.01)

(56) References Cited

U.S. PATENT DOCUMENTS

| | | | |
|---|---|---|---|
| 4,778,247 A | | 10/1988 | Carpenter |
| 4,832,003 A | | 5/1989 | Yabe |
| 4,856,495 A | | 8/1989 | Tohjoh et al. |
| 4,860,732 A | | 8/1989 | Hasegawa et al. |
| 4,918,521 A | * | 4/1990 | Yabe et al. ............. 348/76 |
| 5,089,895 A | * | 2/1992 | Fraker et al. ............ 348/373 |
| 5,376,960 A | | 12/1994 | Wurster |
| 5,379,756 A | | 1/1995 | Pileski et al. |
| 5,418,566 A | | 5/1995 | Kameishi |
| 5,438,975 A | | 8/1995 | Miyagi et al. |
| 5,547,457 A | | 8/1996 | Tsuyuki et al. |
| 5,830,401 A | * | 11/1998 | Prichard et al. ............ 264/262 |
| 5,966,168 A | | 10/1999 | Miyazaki |
| 6,004,263 A | | 12/1999 | Nakaichi |
| 6,110,104 A | | 8/2000 | Suzuki et al. |
| 6,456,863 B1 | | 9/2002 | Levin et al. |
| 7,455,806 B2 | * | 11/2008 | Junger et al. ............ 264/516 |
| 7,758,495 B2 | | 7/2010 | Pease et al. |
| 8,182,422 B2 | | 5/2012 | Bayer et al. |
| 8,547,424 B2 | | 10/2013 | Ishii et al. |
| 2002/0022765 A1 | * | 2/2002 | Belson ............ 600/146 |
| 2003/0056540 A1 | | 3/2003 | Mukasa et al. |
| 2004/0199052 A1 | | 10/2004 | Banik et al. |
| 2005/0075538 A1 | | 4/2005 | Banik et al. |
| 2005/0119527 A1 | | 6/2005 | Banik et al. |
| 2005/0140068 A1 | * | 6/2005 | Junger et al. ............ 264/571 |
| 2005/0154262 A1 | | 7/2005 | Banik et al. |
| 2005/0203341 A1 | | 9/2005 | Welker et al. |
| 2005/0234499 A1 | * | 10/2005 | Olson et al. ............ 606/192 |
| 2006/0178556 A1 | | 8/2006 | Hasser et al. |
| 2007/0129466 A1 | | 6/2007 | Kagawa et al. |
| 2007/0249907 A1 | | 10/2007 | Boulais |
| 2008/0268559 A1 | | 10/2008 | Jung |
| 2009/0209819 A1 | | 8/2009 | Kitagawa et al. |
| 2010/0210905 A1 | | 8/2010 | Takeuchi et al. |
| 2010/0280316 A1 | | 11/2010 | Dietz et al. |
| 2010/0324367 A1 | | 12/2010 | Matsumoto et al. |
| 2012/0029281 A1 | | 2/2012 | Frassica et al. |
| 2012/0165608 A1 | | 6/2012 | Banik et al. |

FOREIGN PATENT DOCUMENTS

| | | | | |
|---|---|---|---|---|
| CN | 101223634 A | | 7/2008 | |
| EP | 0161834 | | 11/1985 | |
| JP | 60-249114 | | 9/1985 | |
| JP | S 63220214 | | 9/1988 | |
| JP | 63-313970 | | 12/1988 | |
| JP | 5-20701 | | 3/1993 | |
| JP | H05207971 | | 8/1993 | |
| JP | 2002-159438 | | 6/2002 | |
| JP | 2003-235787 | | 8/2003 | |
| JP | 2005152043 A | * | 6/2005 | ............ A61B 1/00 |
| JP | 2006-521882 | | 9/2006 | |
| JP | 2007-075355 | | 3/2007 | |
| WO | WO 2007/124211 A2 | | 11/2007 | |
| WO | WO 2010/067765 | | 6/2010 | |

OTHER PUBLICATIONS

Japanese Patent Office, "Notice of Reasons for Rejection," for Application No. 2011-540075, mailed Jul. 2, 2013, 3 pages.
Danish Search Report dated Jul. 10, 2009: Application No. PA200801759 (1 page).
English Translation of Office Action in Chinese application No. 200980156440.3, dated July 15, 2013 (2 pages).
English Translation of Office Action in Chinese application No. 200980156440.3, dated Jul. 23, 2012 (8 pages).
P.R.C. Office, "Notification of Second Office Action" in co-pending Chinese Application No. 200980156440, mailed Mar. 12, 2014, 6 pgs.
International Preliminary Report on Patentability of corresponding PCT application No. PCT/EP09/66728, Jul. 12, 2010, 7 pgs. (references already cited and considered).

* cited by examiner

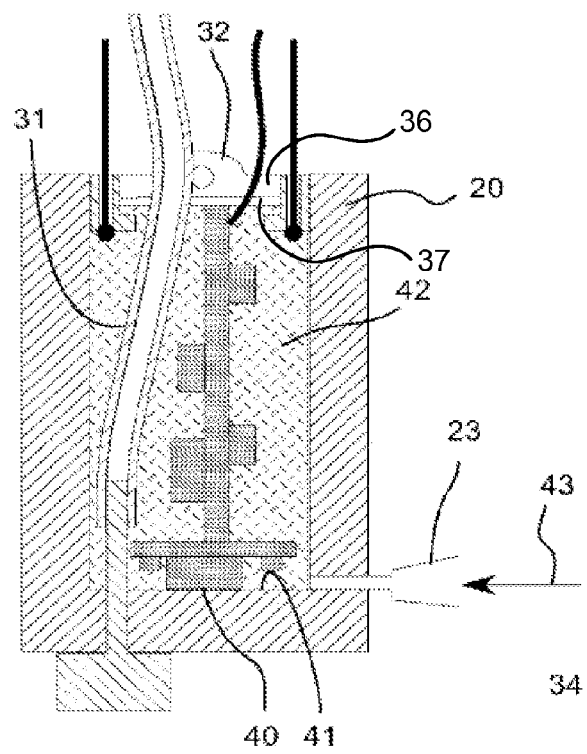
Fig. 4
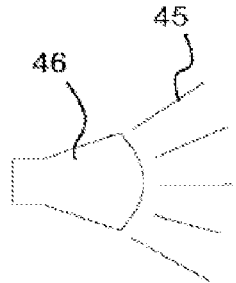
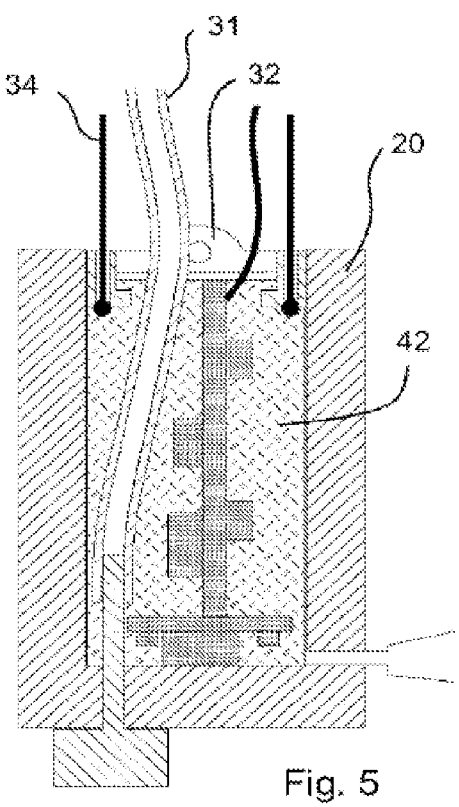
Fig. 5

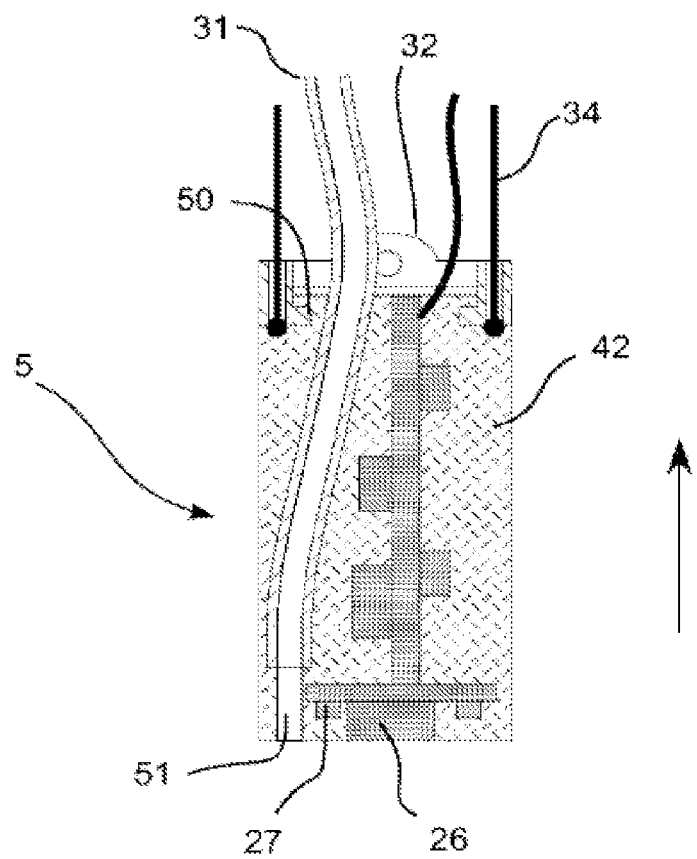
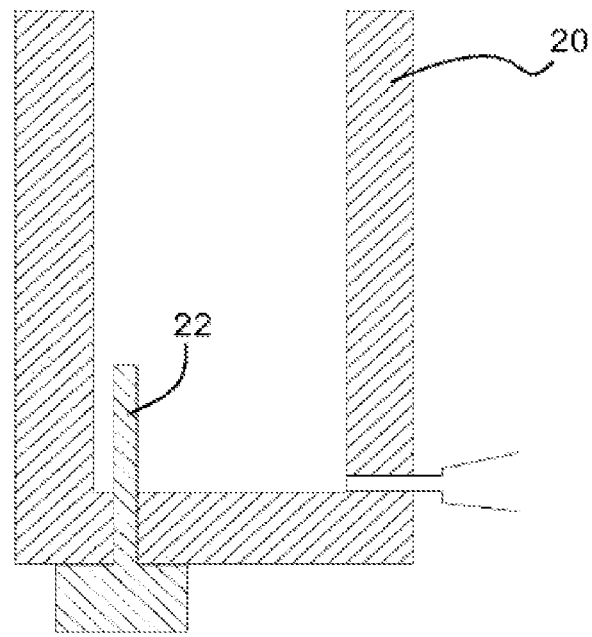
Fig. 6

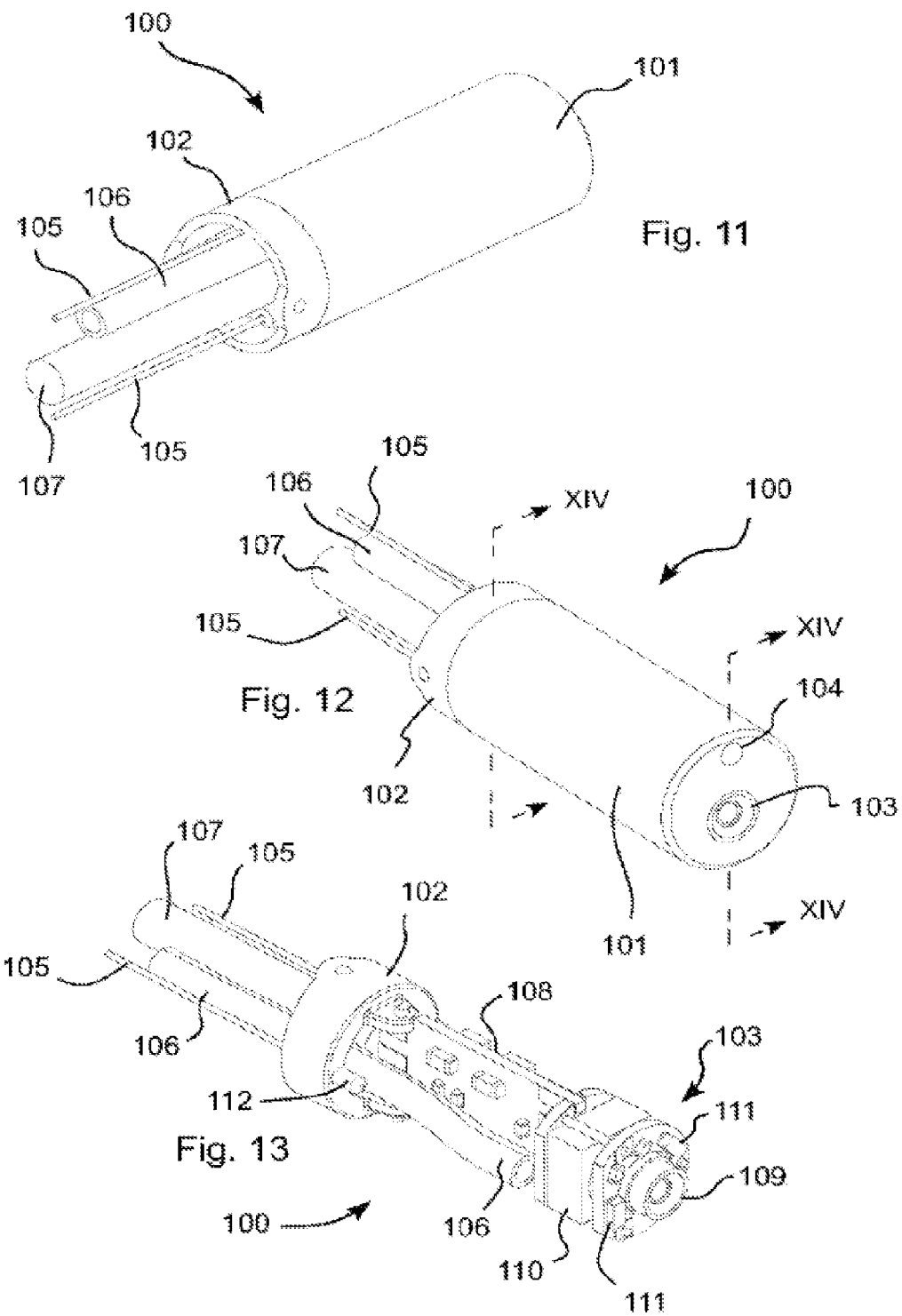

ENDOSCOPE HAVING A CAMERA HOUSING AND METHOD FOR MAKING A CAMERA HOUSING

The current invention relates to an endoscope having a distal end being arranged to be inserted into a body cavity of a patient to be examined and a proximal end which is arranged to be held by the user of the endoscope. The endoscope further comprises a control handle arranged at the proximal end of the endoscope and an insertion portion arranged at the distal end of the control handle. The insertion portion comprises a camera housing arranged at the distal end of the insertion portion, said camera housing being a moulded component comprising an outer surface, a camera device embedded in the material of the camera housing, a light source embedded in the material of the camera housing, an opening at the distal end of the camera housing, and a channel in fluid communication with said opening and where the outer surface of the camera housing and the inner surface of the channel are two surfaces of the moulded camera housing. The endoscope further comprises a tube which provides fluid communication between the proximal end of the channel in the camera housing and a fluid inlet at the proximal end of the endoscope and where the distal end of said tube is arranged at a point between the distal and the proximal end of the camera housing and in that the inner surface of the tube at the distal end of the tube is arranged flush with the inner surface of the channel of the camera housing.

Endoscopes of this kind are well suited to applications which require an endoscope having a tip portion with a very small diameter. The invention also relates to a method of making a camera housing.

In the current specification, the term "moulded component" should cover components which are moulded, ie where a fluid material is injected into a mould and then cured. Note the term fluid in this case should be interpreted as being a material which can flow around objects. For example a powder or a material in granulate form which can be injected into a mould and then hardened would be considered a fluid in the context of the current specification.

The term "outer surface" and "inner surface" when used in the context of this specification should apply to the outer/inner surface respectively of the component being discussed and not the outer/inner surface respectively of the entire endoscope. For example, the "outer surface" of the camera housing as used in the introductory paragraph should be understood as the most external surface of the moulded camera housing itself. If the camera housing were covered with a separate cover member of some sort, for example a thin rubber protection sleeve, the outer surface of the camera housing as understood in this specification would be arranged inside this cover member.

In the current specification, the wording "embedded within the material of the camera housing" should be understood as being surrounded by the material of the camera housing. In other words a component which is embedded within the material of the camera housing is held in place via the material of the camera housing or at least partially surrounded and/or enveloped. Furthermore, embedded should be understood as being in contact with the material. In other words, if the component is placed inside a pre-formed hollow in the material, then this would not be considered to be "embedded" in the context of the current specification. In this specification, the material of the camera housing is poured into the mould in a fluid state whereby the material flows around the components inside the camera housing. In this way, the fluid surrounds the components and when the material cures, the components are embedded within the material of the camera housing. It should be noted that some of the components are fully embedded, ie the fluid entirely surrounds them. Other components are partially embedded, for example the lens of the camera device, where a portion of the camera device is embedded while another part is free of the material. The phrase embedded within the material should therefore not be limited to fully embedded.

DESCRIPTION OF RELATED ART

An example of an endoscope similar to the one mentioned in the opening paragraph is disclosed in U.S. Pat. No. 4,918,521. As can be seen in, for example, FIG. 12 of U.S. Pat. No. 4,918,521, the material of the camera housing holds all the components together. It should be noted that the embodiment according to FIG. 12, is different than the embodiment according to FIG. 5 in the same document. In FIG. 5, a hard outer shell is filled with a material which holds the components of the camera housing. However, in the embodiment of FIG. 12, the material which holds the components in place extends out and forms the outer surface of the camera housing. A mould is required for such a camera housing since the mould determines the outer shape of the camera housing.

While also not being quite the same as the endoscope described in the introductory paragraph, U.S. Pat. No. 5,376,960 discloses a camera housing which could be mentioned in relation to the current invention. In particular FIG. 7 is interesting in that the tubing which provides fluid communication between the control handle and the tip of the endoscope is extended all the way to the tip of the endoscope. However the tip member is formed with a rigid frame 1a,1b arranged inside a hollow tube 2. The frame holds all the components together before the filler material is filed into the hollow tube.

Other endoscopes which share certain features with the endoscope of the current invention are disclosed in FIG. 31 of U.S. Pat. No. 4,745,470 and in FIG. 12 of U.S. Pat. No. 4,832,003.

We note that the current invention is, as mentioned above, related to endoscopes. However, the main focus of the application is on the camera housing of the endoscope. We note that the camera housing is sometimes called the rigid tip portion of the endoscope. The remaining structure of the endoscope is not so relevant for the implementation of the current invention and as such, the remaining structure will not be discussed in great detail in this specification. The person skilled in the art should be able to see how the current camera housing can be integrated into endoscopes of many different forms without any great difficulties.

SUMMARY OF THE INVENTION

It is a first aspect of the current invention to provide an endoscope which is better than the prior art endoscopes. In particular, an aspect of the current invention is to provide an endoscope having a reduced diameter tip portion and to provide a method of assembling an endoscope which is better than the prior art methods.

This aspect is in part provided by an endoscope as mentioned in the opening paragraph but where the endoscope further comprises a bending portion arranged at the distal end of the insertion portion and at the proximal end of the camera housing and where at least the most distal portion of the bending portion is embedded in the material of the camera housing. In this way a camera housing is provided which is easy to assemble with the rest of the bending section.

In one embodiment, the distal end of the tube is arranged between the proximal end of the camera device and the proximal end of the camera housing. In this way, the outer diameter of the camera housing can be reduced since the tubing does not overlap the camera device when seen from the side of the camera housing.

In the case where the bending section is controlled by at least one control wire, one end of the at least one control wire could be embedded in the material of the camera housing. This creates a good connection between the control wire and the camera housing.

In order to increase the speed of production, the material of the camera housing could be chosen as a polymer based material of the kind which cures faster when exposed to UV light.

The material of the camera housing could, in one embodiment be transparent. If the housing is transparent, the light source of the endoscope could then be fully embedded in the material of the camera housing such that the light emitted by the light source passes through at least a portion of the material of the camera housing. This protects the light source from the environment in which the endoscope is inserted. It also makes making the camera housing more simple since the light sources do not have to be very exactly positioned within the mould.

In order to make assembly easier, the camera device could be connected to a frame member and the frame member could be rigidly connected to the distal portion of the bending section before the most distal portion of the bending section is embedded in the material of the camera housing. In this way, the different components of the camera housing can be assembled before they are inserted in the mould cavity. The different components are then held together in a predetermined fashion such that the position of the components in the resulting camera housing can be well determined.

The invention also relates to a method of assembling an endoscope. The method comprises the steps of: placing a camera device and a light source in a mould cavity, said mould cavity having an essentially cylindrical shape and being held in a position such that it has an essentially vertical longitudinal axis, injecting an amount of polymer material in a fluid state into the mould cavity from the bottom of the mould cavity such that the material rises in the mould cavity in a controlled manner, hardening the material and removing the hardened camera housing from the mould cavity.

It should be noted that the above described method describes the steps in their proper order, but other steps could be inserted between, before or after each step or succession of steps.

It should also be mentioned that "essentially cylindrical" as used in this specification should be understood as being cylinder like. This should not be limited to cylinders having a circular cross section, but should be interpreted broadly an encompass square cylinders, rectangular cylinders, and any other form of cylinder.

In a preferred embodiment, the amount of polymer material injected into the mould cavity could be predetermined. In this way, the amount of material in the form can be controlled.

In order to speed up the manufacturing process, the step of hardening the polymer material could comprise the step of applying UV light to the material. In this case, the polymer material is chosen to be of the kind which cures faster when exposed to UV light.

In one embodiment, the method could further comprise the step of placing a flexible tube in said mould cavity and connecting the end of the tube to a cylindrical protrusion which is a part of the mould and which protrudes from the bottom of the mould cavity in a direction parallel to the longitudinal axis of the mould cavity. In this way, a channel can be formed in the material of the camera housing when the protrusion is removed after the material has hardened.

In order to form a strong connection between the bending portion and the camera housing, the method could further comprise the step of placing the most distal portion of a bending section of the endoscope in the mould cavity before injecting the polymer material into the mould cavity. If the bending portion is controlled by at least one control wire, the method could further comprise the step of placing one end of the at least one control wire of a bending portion of the endoscope in the mould cavity before injecting the polymer material into the mould cavity. In this way, the control wire will also have a strong connection to the camera housing. In the case where the distal portion of the bending portion is held together with the camera housing via the material of the camera housing, the remaining segments of the bending portion can be connected to the most distal segment of the bending portion once the camera housing has been removed from the mould. The remaining segments could also have been connected to the most distal segment before the most distal segment was placed in the mould. In this way, the bending portion could be completely assembled first, then put into the mould.

The method could also be arranged such that when the camera device is placed in the mould cavity, the most distal part of the camera device is arranged within a depression in the bottom of the mould cavity, such that the most distal part of the camera device is arranged in the mould at a location which is lower than the lowest level of the mould cavity which will be in contact with the material of the camera housing when the material is injected into the mould cavity. In this way, the position of the camera device within the mould cavity can be more easily determined.

In order to make the step of applying UV light to the material of the camera housing easier, the material of which the mould is made could be chosen to be transparent.

It should be emphasized that the term "comprises/comprising/comprised of" when used in this specification is taken to specify the presence of stated features, integers, steps or components but does not preclude the presence or addition of one or more other features, integers, steps, components or groups thereof. For example, the endoscope according to claim 1 comprises "a channel". However, according to this specification, any number of channels would be covered by the scope of the claims, as long as there was at least one channel.

BRIEF DESCRIPTION OF THE DRAWINGS

In the following, the invention will be described in greater detail with reference to embodiments shown by the enclosed figures. It should be emphasized that the embodiments shown are used for example purposes only and should not be used to limit the scope of the invention.

FIGS. 2-6 schematically show different steps of a first method of assembling an endoscope according to the invention.

FIGS. 11 and 12 show more detailed perspective views of the camera housing of the endoscope.

FIG. 13 shows a perspective view of the camera housing as shown in FIG. 2, but where the housing itself has been removed in order to show the interior components. Note that the figure is rotated 90° about its longitudinal axis with regards to FIG. 12.

DETAILED DESCRIPTION OF THE EMBODIMENTS

Figure 1:
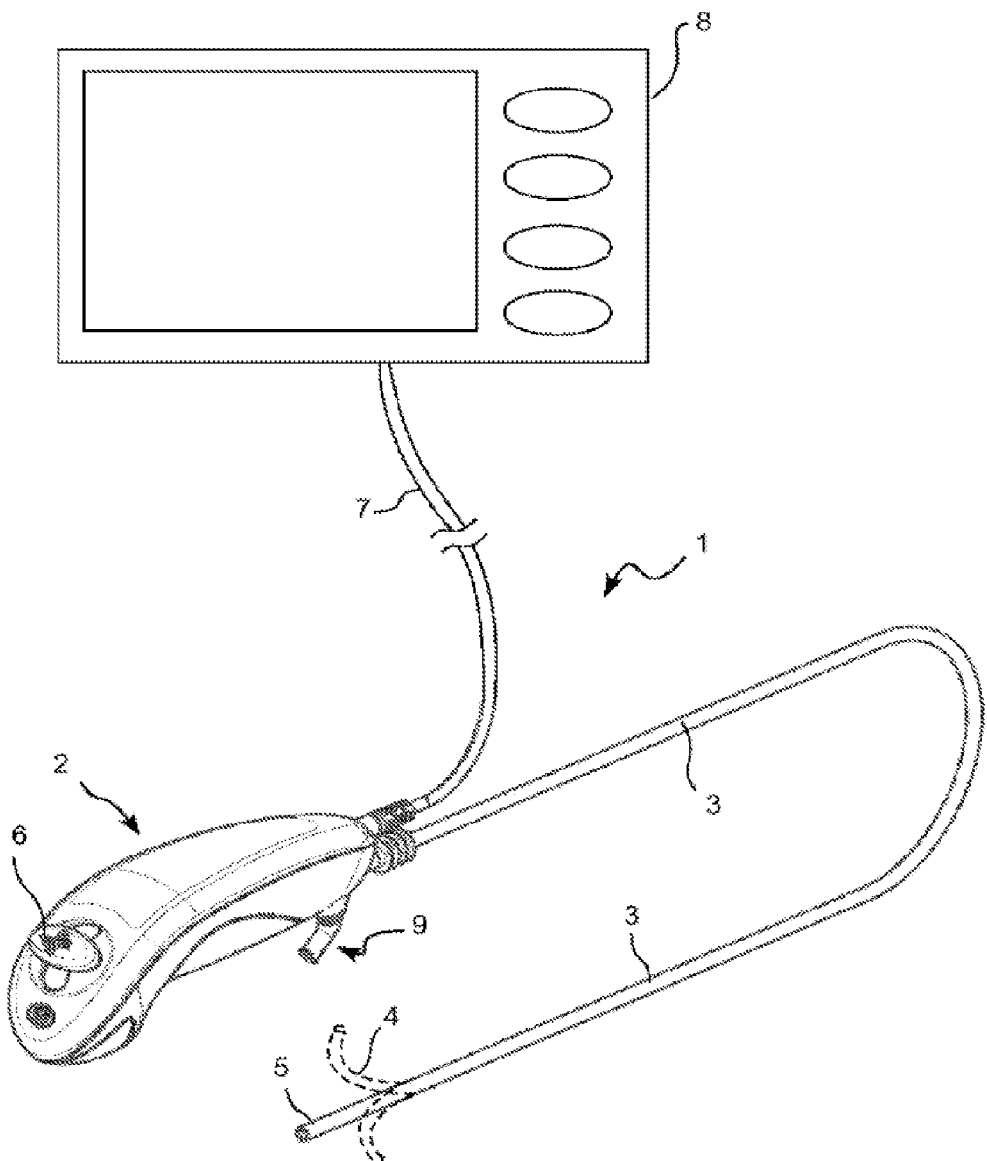
FIG. 1 shows a complete perspective view of an endoscope according to the invention as well as schematic views of supporting equipment.

The endoscope 1 shown in FIG. 1 comprises a control handle 2, a flexible insertion portion 3, a bending portion 4 and a rigid tip portion 5. The control handle comprises a joystick 6 which is connected to the bending portion via control wires (not shown) arranged partly within the control handle, the flexible insertion portion and the bending portion. When the joystick is activated, the bending portion bends as shown by the dashed lines in FIG. 1. The control handle further comprises an electrical cable 7 which is used to connect the endoscope to a control module 8. In this embodiment the control module comprises a power source and a video monitor 8. The endoscope further comprises an injection port 9 which is in communication with an opening 104 (see FIG. 12) at the distal end of the rigid tip portion (camera housing) of the endoscope. The injection port 9 can be used to inject fluids into the endoscope which will be sprayed out at the opening at the tip of the endoscope. This could for example be a local anaesthetic or the like.

The flexible insertion portion 3 is arranged as a tube which is flexible and therefore bendable. However, the flexible insertion portion is stiff in the longitudinal and in the torsional direction. In this way, rotation of the control handle is transferred directly to the tip and allows the user of the endoscope to control the rotational position of the tip of the endoscope by twisting the control handle. A camera 109 and a light source 111 (see FIG. 13) are arranged in the rigid tip portion 5 of the endoscope. The rigid tip portion is therefore often called a camera housing. The electrical signals from the camera and the power to the camera and the light source are transferred via wires (not shown) arranged partly within the control handle, the flexible insertion portion and the bending portion of the endoscope. The flexible insertion portion, the bendable section and the camera housing/rigid tip portion are typically covered with a thin elastic covering which protects the components. This is why in the figures, there is no visible transition between the flexible insertion portion 3, the bendable section 4 and the rigid tip portion 5.

It should be noted that endoscopes comprising the above mentioned features are very well known to the person skilled in the art and further details will not be required by the person skilled in the art to understand and implement the current invention. The main invention disclosed in the current application is directed to the camera housing and to a method of producing said camera housing.

It should also be noted that in certain cases, the endoscope is described as having a control handle and an insertion portion. The control handle is held by the user of the endoscope and the insertion portion is inserted into a patients body cavity. According to this definition, the embodiment shown in FIG. 1 comprises an insertion portion which comprises a flexible insertion portion 3, a bending portion 4 and a rigid tip portion 5. The bending portion and the rigid tip portion are therefore arranged near or at the distal end of the insertion portion.

We also note that in the current specification, the example endoscope shown in FIG. 1 is an endoscope used to help in establishing artificial respiration for patients. An endotracheal tube is placed over the flexible insertion portion of the endoscope and the flexible insertion portion is then inserted into the airway of a patient. The vision system in the tip of the endoscope allows the endoscope to be guided into place without danger for the patient. Once the endoscope and the endotracheal tube are in place, the endoscope can be withdrawn leaving the endotracheal tube in place in the airway of the patient. While this is the only concrete embodiment of an endoscope disclosed in this specification, it should be understood that the teachings of the current specification can apply to many other types of endoscopes as well.

As one non-limiting example, the endoscope shown in the figures comprises a flexible insertion portion and a bendable section. However, a camera housing according to the current invention could also be used with an endoscope having a stiff insertion portion and/or without a bendable section.

One embodiment of a method of manufacturing a camera housing according to the current invention is described with regards to FIGS. 2-6.

Figure 2:
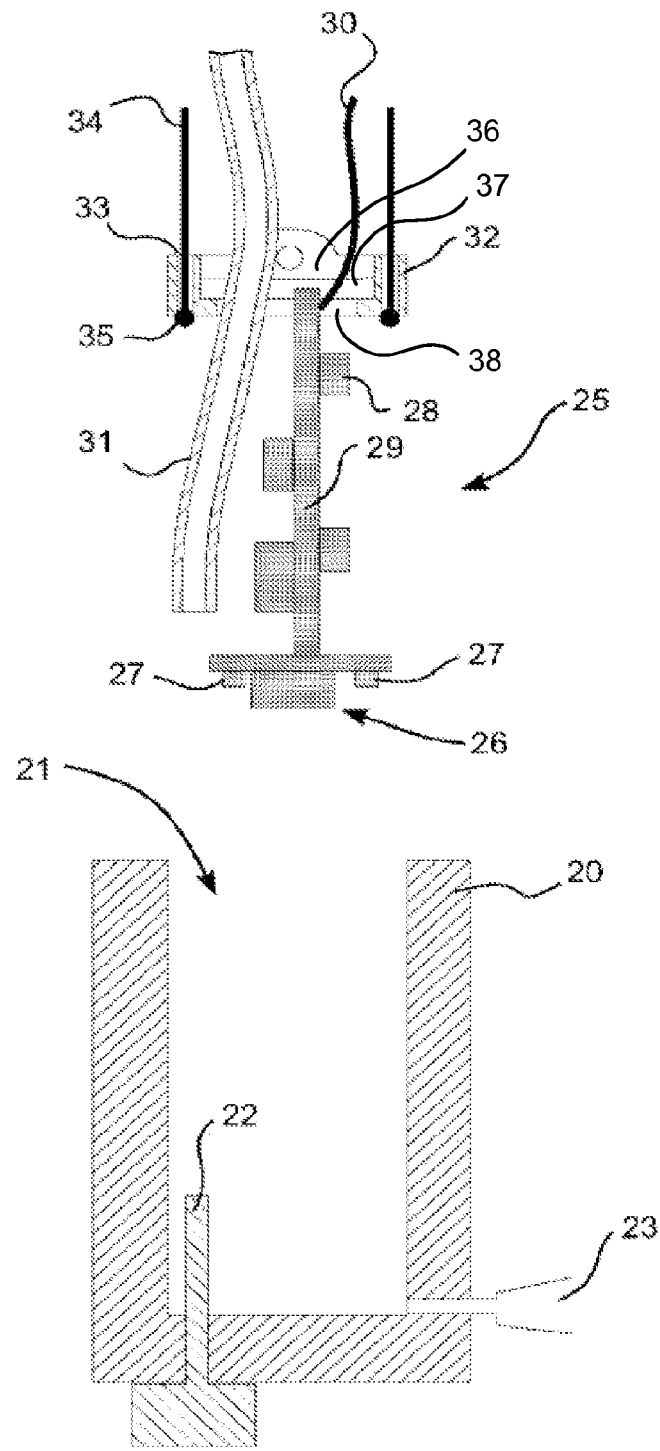

FIG. 2 shows a schematic representation of a mould 20 having a mould cavity 21. A removable protrusion 22 is arranged in the bottom of the mould cavity. An inlet 23 is provided in the mould cavity for injecting fluid material into the mould cavity. FIG. 2 also shows a small electronic circuit 25. The electronic circuit comprises a camera device with a lens 26, two light sources 27 (in this case LEDs), and associated electronic components 28 arranged on a support structure/PCB 29. A wire 30 connects the electronic circuit 25 with the control handle at the proximal end of the endoscope. The wire 30 supplies power to the electronic circuit 25 and feeds the image signals from the camera to the control handle. From the control handle the image signals are sent to a control module which can process the signals such that they can be displayed on a video display.

A flexible tube 31 is also shown in FIG. 2. The flexible tube is connected to the injection port 9 at the control handle. The flexible tube is sometimes referred to as a "working channel". The flexible tube is used to transfer fluid injected at the control handle (i.e. at the proximal end of the endoscope) to the distal end of the endoscope.

FIG. 2 also shows the most distal segment 32 of an articulated bending portion 4 configured as a connecting portion. The segment 32 comprises a peripheral wall 36, a central hollow portion 38 therethrough, two channels 33 for accepting a control wire 34 each, and a cut-out 37 on the peripheral wall. The control wires are connected to a control mechanism arranged in the control handle of the endoscope and are used to control the bending of the bending portion. The control wires are fastened to the most distal segment of the bending portion. In the case of this embodiment, the control wires are each fastened to each their own stopper element 35 which is larger than the channels 33 of the most distal segment of the bending portion. In this way, the wires cannot pull through the segment.

In the current embodiment, the support structure/frame/PCB of the electronic circuit is fastened to the most distal segment 32 of the bending portion before the components are inserted in the mould cavity. In this way, the electronic circuit and the most distal segment of the bending portion can be manipulated as one single unit. Furthermore, the flexible tube 31 and the signal wire 30 are arranged to pass through a central hollow portion of the segment of the bending portion.

Figure 3:
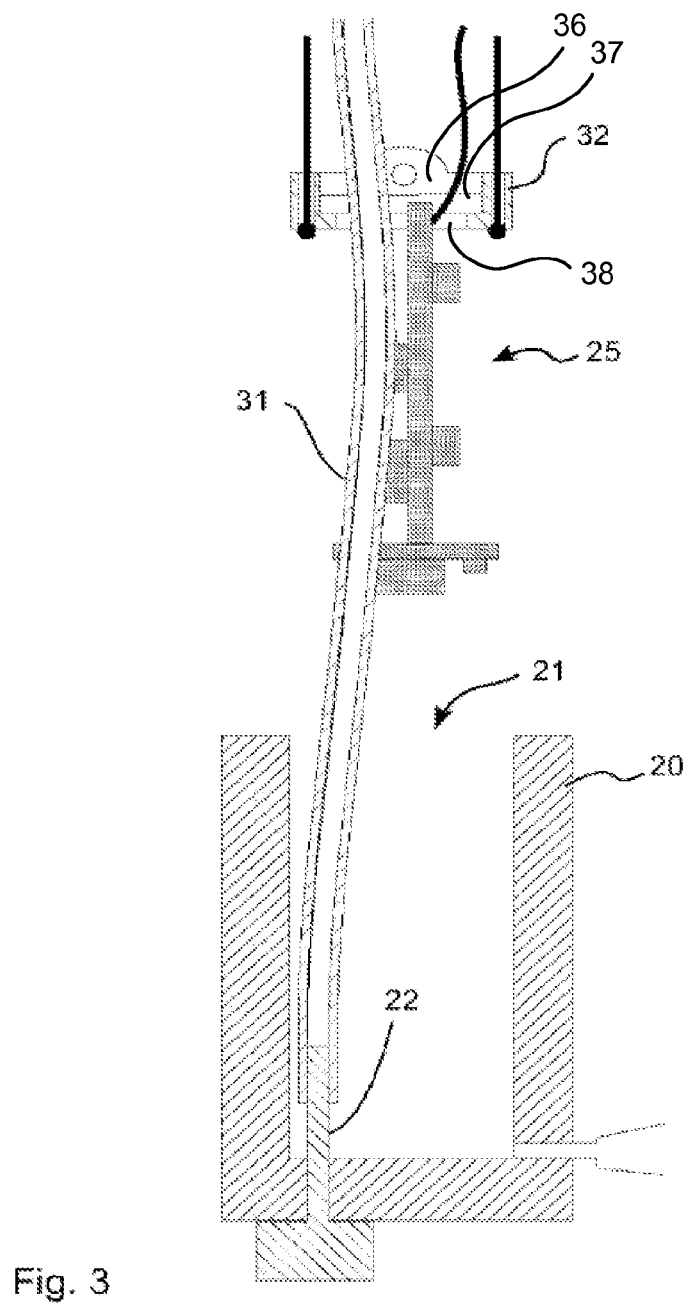

FIG. 3 shows the next step in the process. In this step, the distal end of the flexible tube 31 has been connected to the protrusion 22 protruding from the bottom of the mould cavity. The protrusion 22 is arranged to have an outer diameter which is essentially equal to the inner diameter of the flexible tube. The tube is held in place by friction. The tube is placed over the protrusion, but is not extend all the way to the bottom of the mould cavity. As can be seen from the next figure, the tube is placed such that the distal end of the tube will be slightly behind (more proximal) the camera device.

FIG. 4 shows the next two steps in the process. First the combined unit of the electronic circuit and the most distal segment of the bending portion is put into the form and the most distal portion 40 of the camera device is pressed against the bottom surface 41 of the form. A liquid polymer material 42 is then injected into the mould cavity via the inlet 23 as shown by the arrow 43. The material could be one of many different types of materials. Two non-limiting examples are a UV curing epoxy or an acrylic casting compound. The amount of liquid polymer material is predetermined before injecting the material. By injecting the material into the bottom of the mould, the material will slowly rise in the cavity and a controlled filling will be provided with a low risk of forming any air pockets in the bottom of the cavity. As can be seen from FIG. 4, the amount of material injected into the form is chosen such that the entire electronic circuit as well as the connection between the signal wire and the electronic circuit are embedded in the material. In addition, the most distal segment of the bending portion as well as the ends of the control wires are also embedded in the material of the camera housing. A distal portion of the flexible tube 31 is also embedded in the material of the camera housing.

In FIG. 5, UV light 45 is shown being applied to the mould via a UV light source 46. The mould is formed from a transparent material which allows the material in the mould cavity to be exposed to UV light. The material in the mould cavity is also chosen to be of the kind which responds to UV light by curing more quickly. In this way, the fluid material which is injected into the mould can be cured very quickly. Instead of making the mould transparent, it could also be imagined that the UV light is shone through the central hollow of the most distal segment of the bending portion. Or a portion of the mould could be made transparent, for example the bottom surface of the mould.

FIG. 6 shows the last step of the process where the cured component is removed from the mould. It should be noted that the material of the mould can be chosen to be of a kind which allows the material of the camera housing to easily release from the mould. Or a mould release agent such as teflon can be applied to the inside of the mould before injecting the fluid material. The mould could furthermore be made from a flexible material itself, for example silicon rubber whereby the mould could be stretched, thereby easily allowing the cured camera housing to be removed from the mould.

It should be noted from FIG. 6 that in the current embodiment of the resulting camera housing, the light sources 27 are fully embedded within the material of the camera housing. This is possible by making the material of the camera housing transparent. In this way, the light from the light source will shine through the material of the camera housing.

It should also be noted from FIG. 6, that the most distal segment of the bending portion is formed with a protruding portion 50. In the current example, the protruding portion 50 is in the shape of a hook when seen in a cross section as shown in FIG. 6. This hook portion is actually a circular ledge which protrudes from the entire inner periphery of the most distal segment of the bending portion. It can also be seen that the amount of material put into the cavity is chosen such that the "hook" portion is covered by the material of the camera housing. In this way, there is a positive connection between the most distal segment of the bending portion and the material of the camera housing. This type of protruding portion could be formed in many other ways and does not necessarily have to be in the form of a hook. However, in the case where the material of the camera housing and the material of the most distal segment of the bending portion do not bind so well, a mechanical attachment between the two components could be beneficial.

It can also be seen from FIG. 6 that when the camera housing is removed from the mould, the protrusion is also removed from the camera housing. In this way, a channel 51 is formed in the camera housing. This channel has the same inner diameter as the inner diameter of the flexible tube 31. In this way there is no step at the transition between the flexible tube and the channel.

Figure 7:
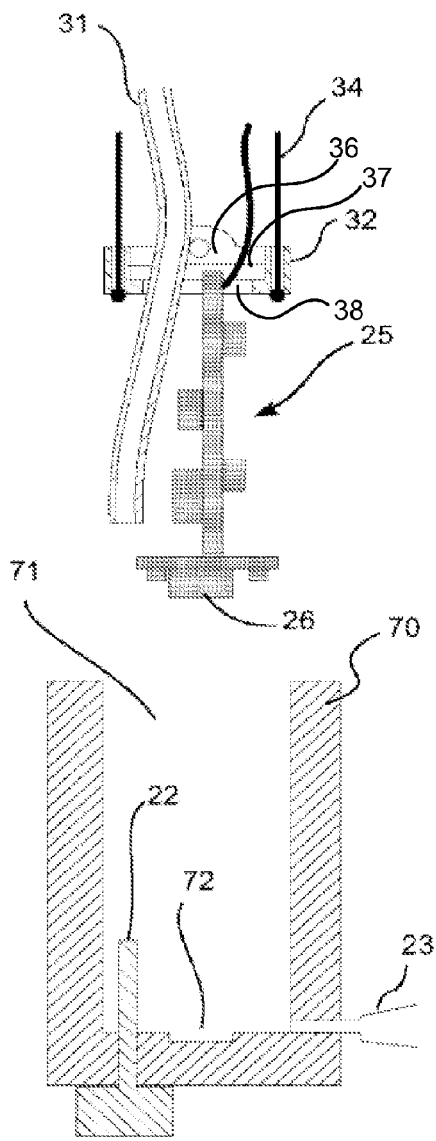
FIGS. 7-8 schematically show two steps of a second embodiment of a method of assembling an endoscope according to the invention.
Figure 8:
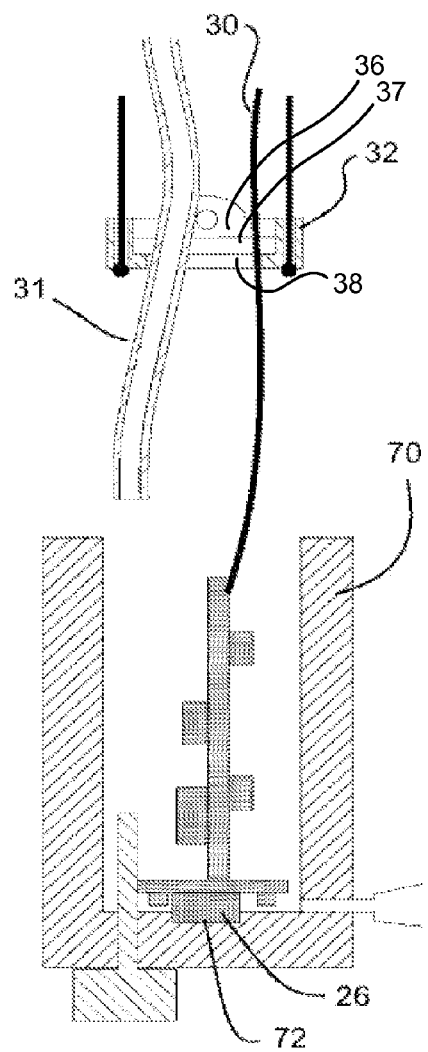

FIG. 7 shows two steps of a second embodiment of a process according to the current invention. In contrast to FIGS. 2 and 3, the mould 70 of this embodiment is slightly different from the mould 20 of the first embodiment. In this embodiment, the mould cavity 71 is formed with a depression 72 in the bottom of the mould cavity. The depression 72 is shaped and sized to accept the most distal portion of the camera device. In this way, the electronic circuit comprising the camera device can be arranged in the mould cavity and be precisely placed with respect to the mould cavity without any need for it to be connected to the most distal segment of the bending portion before being inserted into the mould cavity. This is shown in FIG. 8 where the electronic circuit has been inserted into the mould cavity, but the flexible tube and the most distal portion of the bending portion are not yet inserted. In the next step, the flexible tube would be connected to the protrusion and then the most distal segment of the bending section would be placed in the form.

Figure 9:
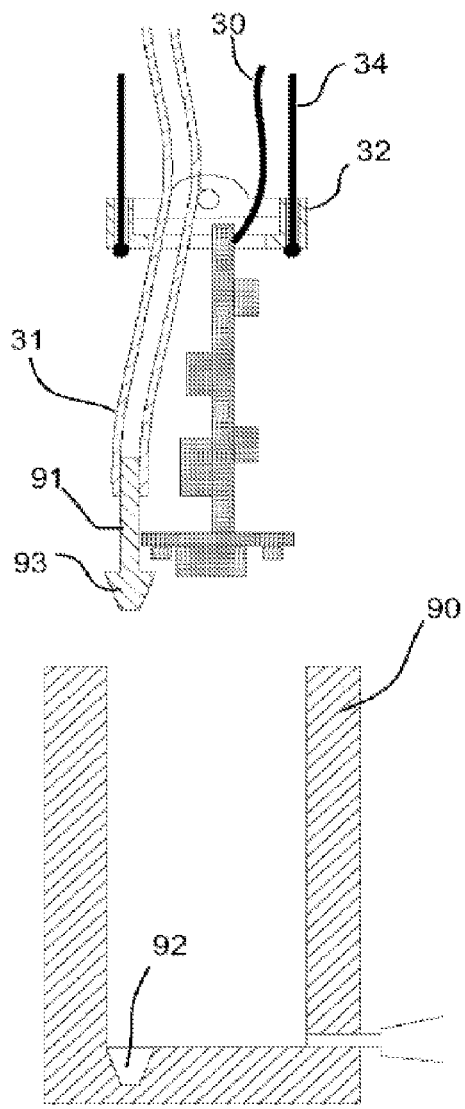
FIGS. 9-10 schematically show two steps of a third embodiment of a method of assembling an endoscope according to the invention.
Figure 10:
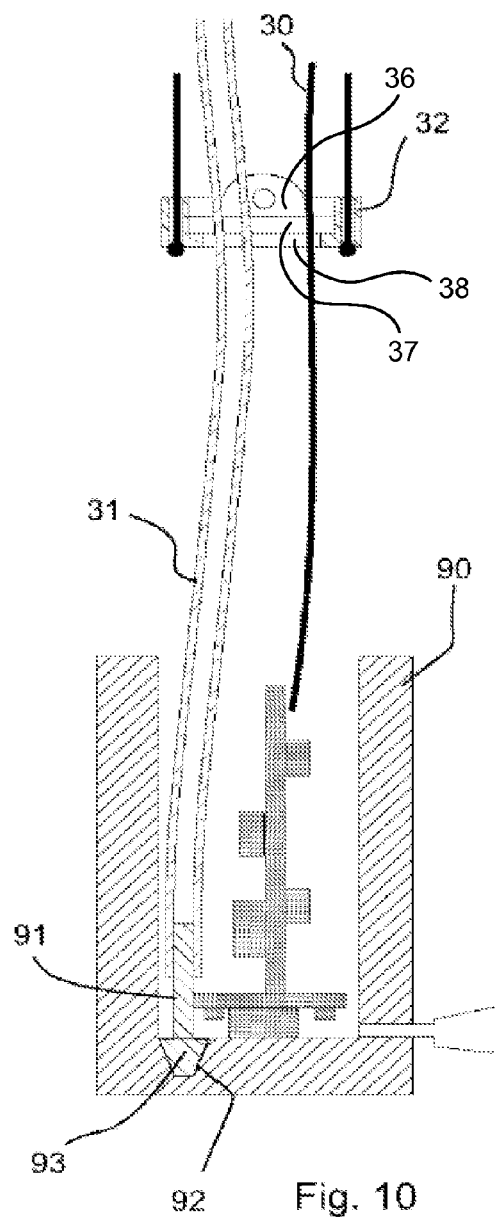

FIGS. 9 and 10 also show an alternative method of the process shown in FIGS. 2-6. In this embodiment, a pin 91 is inserted in the end of the flexible tube before the tube is placed in the mould 90. The outer diameter of the pin 91 is essentially the same as the inner diameter of the flexible tube. The electronic circuit is then placed in the mould cavity followed by the flexible tube.

When inserting the flexible tube, the pin is inserted into a hole 92 in the bottom of the mould cavity. After filling the mould with the material of the camera housing and removing the cured camera housing from the mould cavity, the pin can be removed from the camera housing. In order to make it easier to insert the pin in the hole in the bottom of the mould cavity, the end of the pin 93 and the hole are formed as corresponding cones which taper in the direction towards the bottom of the mould cavity.

As can be imagined by the person skilled in the art, the methods described above have many different variants and many different types of camera housings can be made according to the disclosed methods. However, FIGS. 11-17 show some different views of one concrete embodiment 100 of a camera housing manufactured according to a method similar to the ones described above.

The camera housing as shown in FIGS. 11-12 comprises a main body portion 101, a most distal segment 102 of an articulated bending portion, a camera device 103, an opening 104 at the distal end of the camera housing, two control wires 105, a flexible tube 106 and an electrical wire 107. The main body portion is made from a transparent polymer material which is poured into a mould cavity after the other components have been placed in the mould cavity. Once the polymer material has been completely injected, the material is cured and the main body portion removed from the mould. The main body portion is therefore solid and the components arranged inside the main body portion are embedded either completely (such as the LEDs) or partially (such as the flexible tube and the camera device) within the material of the main body portion.

FIG. 13 shows the camera housing as shown in FIG. 12 but where the main body portion has been hidden in order to be able to see the inner details of the camera housing. This would be the situation just before the material of the main body portion is injected into the mould. In FIG. 13 one can see the electronic circuit 108 which controls the camera device 103 and provides basic signal conditioning. The camera device is comprised of a lens 109 and the camera chip itself 110. Light sources 111 in the form of two LEDs are arranged around the lens. As can be seen in FIG. 13, the electrical components are all packaged together in a type of frame which holds all the components together. In this example, the frame is a PCB. This frame is attached to the most distal segment 102 of the bending portion before the assembly is placed in the form. In this way, the most distal segment of the bending portion and the electronic circuit can be assembled into a complete unit which can be handled in a simple manner. Very little assembly is required in the actual mould.

FIG. 13 also shows how the control wires 105 are attached to the most distal segment 102 of the bending portion. In this embodiment, a stopper element 112 is fastened to the ends of the control wires. The diameter of the stopper element is larger than the inner diameter of the channels in the most distal segment of the bending portion. The control wires can therefore not pull through these channels. When the material of the main body portion is poured into the mould cavity, these stopper elements are also embedded in the material of the main body portion and are even more firmly held fast to the most distal segment of the bending portion.

Figure 14:
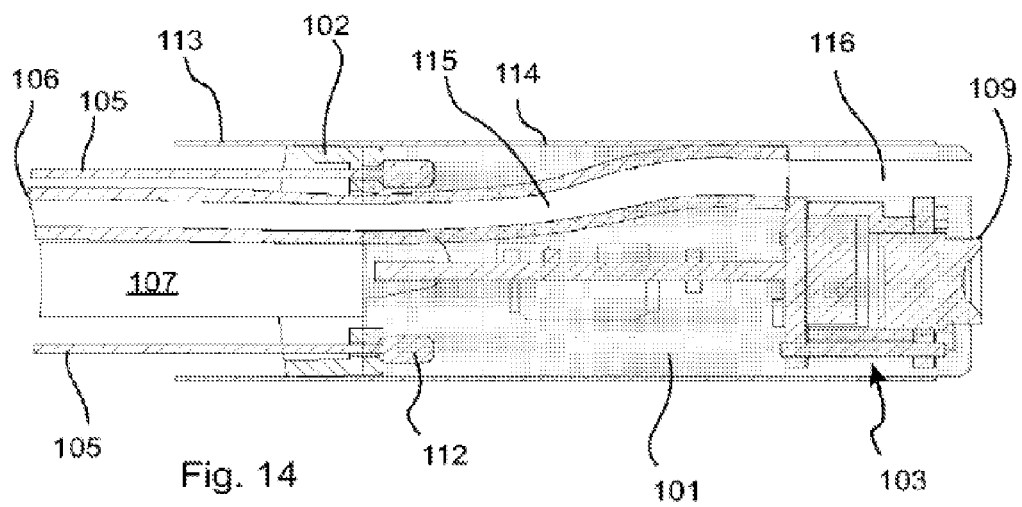
FIG. 14 shows a cross section through the camera housing according to the line XIV-XIV defined in FIG. 12.
Figure 15:
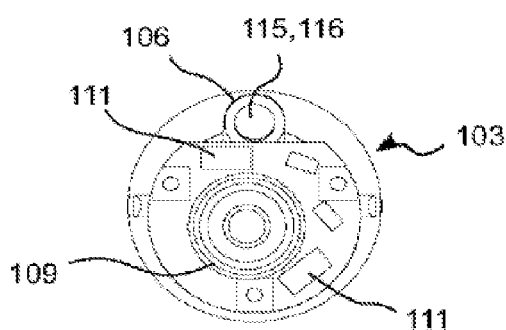
FIG. 15 shows a front view of the camera housing as shown in FIG. 13.
Figure 16:
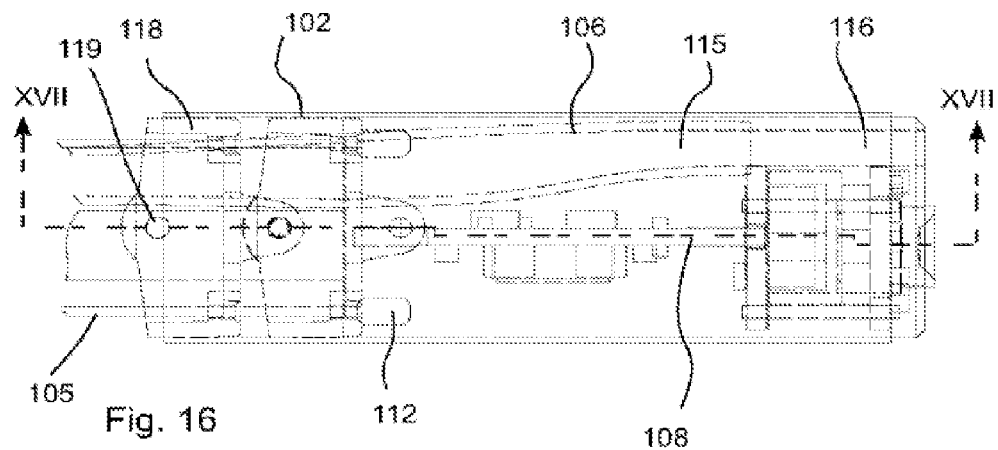
FIG. 16 shows a side view of the camera housing shown in FIG. 12, and where the interior components are shown with hidden lines.

As can be seen in FIG. 14, the main body portion 101 is covered by an elastic cover member 113. In the current embodiment, the cover member covers the camera housing, the bending section and the flexible insertion portion.

It can also be seen in FIG. 14, that the flexible tube 106 is arranged near the outside surface 114 of the camera housing. In this case, the outside surface 114 is arranged on the inside of the cover member 113. The tube is arranged in the main portion of the camera housing so that the distal end of the tube is arranged behind (ie in the direction towards the proximal end of the endoscope) the camera device 103. Furthermore, it can be seen that the thickness of the tube is such that the camera device overlaps the wall thickness of the flexible tube. This can be better seen in FIG. 15 which shows the front of the camera housing where the material of the main body portion has been removed. This arrangement of the flexible tube behind the camera device allows the outer diameter of the camera housing to be made smaller. In the current embodiment, the outer diameter of the camera housing is only about 5 mm and the thickness of the elastic cover member is only about 0.1 mm. The resulting outer diameter is therefore 5.2 mm in the current embodiment.

As can also be seen in FIG. 14, the channel 115 of the flexible tube is continued past the camera device via a channel 116 arranged in the material 101 of the main body portion of the camera housing. This channel is formed as described above by a protrusion in the mould in which the camera housing is formed. The protrusion is removed from the camera housing after the camera housing has cured leaving the channel behind. The inner diameter of the channel 116 in the main body portion is arranged to be the same as the inner diameter of the channel 115 in the flexible tube. In this way there is no step at the transition between the flexible tube and the channel in the material of the main body portion.

Figure 17:
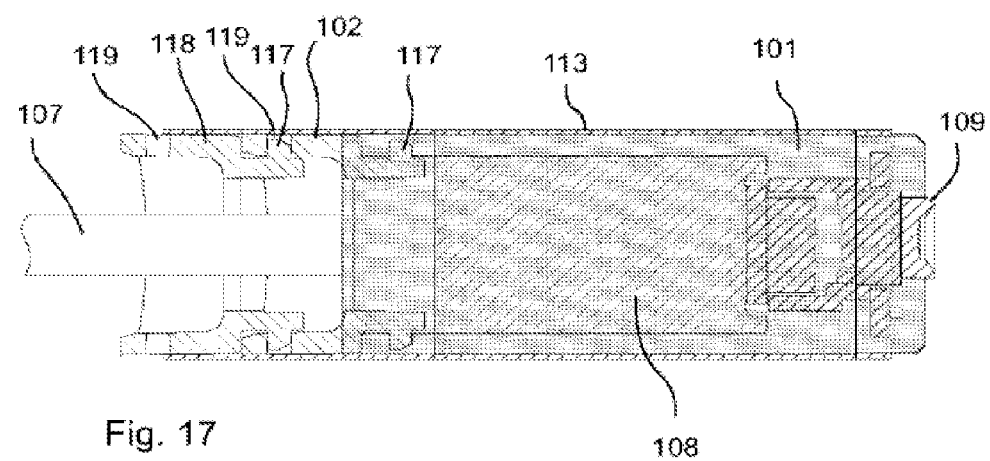
FIG. 17 shows a cross section view through the camera housing according to the line XVII-XVII defined in FIG. 16.

From FIG. 17, it can be seen that the material of the main body portion also embeds the hinge pins 117 of the most distal segment 102 of the bending portion. In this way there is a positive connection between the material of the main body portion of the camera housing and the most distal segment of the bending portion. The hinge pins can be considered to be a sort of hook portion which makes a mechanical connection between the most distal segment of the bending portion and the material of the main body portion of the camera housing.

FIG. 17 also shows the next most distal segment 118 of the bending section engaged with the most distal segment 102 of the bending portion. As can be seen the proximal part of each segment 102,118 of the bending portion comprises a recess 119 in which the hinge pins 117 on the distal portion of the segment engage.

It is to be noted that the figures and the above description have shown the example embodiments in a relatively simple and schematic manner. Many of the internal electronic and mechanical details have not been shown in great detail since the person skilled in the art should be familiar with these details and they would just unnecessarily complicate this description.

Furthermore, the person skilled in the art will understand that additional embodiments are derivable from the teachings of this specification and that these embodiments should also be included within the scope of protection. For example, in the current embodiments, the bending portion has been an articulated bending portion comprising a number of articulated segments. However, an embodiment with a single piece bending portion could also be imagined.

It should also be noted that the current claim set has focussed on some particular features, but the person skilled in the art will understand that divisional applications could be filed directed to other features. For example, the current independent claim 1 is directed to an endoscope with a bending portion and where at least a portion of the most distal segment of the bending portion is embedded within the material of the camera housing. But a divisional application could be filed directed at an endoscope without a bending portion, for example, by focussing on the arrangement of the LEDs which are fully embedded within the material of the camera housing. It should also be noted that the product claim is currently limited to an endoscope with a bending portion, but the method claim is not limited in the same way.

The invention claimed is:

1. A method of assembling an endoscope, said method comprising:
 placing a camera device having a lens, a light source, an electronic component, and an electrical conductor onto a support structure in a mould cavity of a mould, said mould cavity having an open end and a bottom with a bottom surface opposite the open end;

fastening a distal end of a control wire to a connecting portion of a bending portion of the endoscope, the control wire configured to articulate the bending portion of the endoscope, the connecting portion including two wire channels, a peripheral wall, a central hollow portion therethrough, and a cut-out on the peripheral wall between the two wire channels, wherein fastening the distal end of the control wire comprises passing the distal end of the control wire through one of the two wire channels;

placing the connecting portion and a distal end of a flexible tube in the mould cavity, the distal end of the flexible tube extending distally beyond the connecting portion;

injecting an amount of polymer material in a fluid state into the mould cavity from the bottom of the mould cavity such that the polymer material rises in the mould cavity toward the open end to at least partially embed in the polymer material the distal end of the flexible tube, the connecting portion, the distal end of the control wire, and the camera device, thereby causing a portion of the polymer material to flow transversely along the connecting portion to form a positive connection;

hardening the polymer material to form a camera housing, wherein the positive connection includes the cut-out of the connecting portion and the hardened polymer material; and removing the camera housing from the mould cavity.

2. The method according to claim 1, wherein said amount of polymer material injected into the mould cavity is predetermined.

3. The method according to claim 1, wherein hardening the polymer material comprises applying UV light to the polymer material.

4. The method according to claim 3, wherein the mould is transparent, and wherein hardening the polymer material comprises applying UV light to the polymer material through the mould.

5. The method according to claim 1, wherein placing the camera device and the light source in the mould cavity comprises placing a most distal part of the camera device within a depression in the bottom of the mould cavity, such that the most distal part of the camera device is arranged in the mould at a location which is lower than a lowest level of the mould cavity which will be in contact with the polymer material of the camera housing when the polymer material of the camera housing is injected into the mould cavity.

6. The method according to claim 1, wherein the polymer material of which the mould is made is transparent.

7. The method according to claim 1, further comprising connecting the camera device to a frame member and rigidly connecting the frame member to the connecting portion before injecting the amount of polymer material.

8. The method according to claim 1, wherein fastening a distal end of a control wire comprises securing a stopper element to the distal end of the control wire to prevent the control wire from pulling through the wire channel.

9. The method according to claim 1, wherein the flexible tube does not overlap the camera device when seen from a side of the camera housing, thereby enabling the camera housing to have a reduced cross-section.

10. The method according to claim 9, wherein a radial distance between an inner surface of the flexible tube and an outer surface of the camera device is less than a wall thickness of the flexible tube.

11. The method according to claim 1, further comprising inserting a pin into the distal end of the flexible tube before placing the distal end of the flexible tube in the mould cavity, and inserting the pin into a hole in the bottom of the mould before injecting the polymer material into the mould cavity.

12. The method according to claim 1, further comprising passing the flexible tube through the central hollow portion of the connecting portion.

13. The method according to claim 1, wherein the bending portion of the endoscope includes a plurality of segments including the connecting portion, further comprising connecting the plurality of segments before placing the connecting portion in the mould cavity.

14. The method according to claim 1, further comprising placing the distal end of the flexible tube over a protrusion extending from the bottom of the mould cavity toward the open end of the mould cavity to form a working channel in the camera housing after removing the camera housing from the mould cavity.

15. The method of claim 1, wherein the connecting portion includes a protruding portion, and wherein injecting the polymer material into the mould cavity includes at least partially surrounding the protruding portion with the polymer material.

16. The method of claim 15, wherein the protruding portion is a ledge that protrudes from an inner periphery of the connecting portion, wherein injecting the polymer material comprises fully embedding the ledge in the polymer material.

17. A method of assembling an endoscope, the method comprising:
placing a camera device having a lens, a light source, an electronic component, and an electrical conductor onto a support structure in a mould cavity of a mould, said mould cavity having an open end and a bottom with a bottom surface opposite the open end, wherein the mould allows passage of UV light;
placing in the mould cavity a first end of a control wire configured to articulate the bending portion of the endoscope;
placing in the mould cavity a distal end of a flexible tube;
placing in the mould cavity a connecting portion of a bending portion of the endoscope, the connecting portion including a peripheral wall and a ledge protruding therefrom,
injecting polymer material in a fluid state into the mould cavity from the bottom of the mould cavity to at least partially embed in the polymer material the first end of the control wire, the distal end of the flexible tube, the camera device, the light source, and the ledge, thereby causing a portion of the polymer material to flow transversely along said protruding ledge to form a positive connection;
removing the camera housing from the mould cavity.

18. The method according to claim 17, wherein the flexible tube does not overlap the camera device when seen from a side of the camera housing, thereby enabling the camera housing to have a reduced cross-section.

19. A method of assembling an endoscope, the method comprising:
connecting a camera device, a light source, a support structure and a distal end of a control wire to a connecting portion of a bending portion of the endoscope to form an assembly, the control wire configured to articulate the bending portion of the endoscope, the connecting portion including a peripheral wall and a ledge protruding therefrom;
placing the assembly in a mould cavity of a mould;
placing a distal end of a flexible tube in the mold cavity;
injecting polymer material in a fluid state into the mould cavity from the bottom of the mould cavity to at least partially embed the assembly, the distal end of the flexible tube, and the ledge, thereby causing a portion of the polymer material to flow transversely along said protruding ledge to form a positive connection;

hardening the polymer material to form a camera housing, wherein the positive connection includes said assembly and the hardened polymer material; and removing the camera housing from the mould cavity.

* * * * *